US011426121B1

(12) United States Patent
Castellano et al.

(10) Patent No.: US 11,426,121 B1
(45) Date of Patent: Aug. 30, 2022

(54) SEMI-AUTOMATED PLANTAR SURFACE SENSATION DETECTION DEVICE

(71) Applicants: Auburn University, Auburn, AL (US); Edward Via Virginia College of Medicine, Auburn, AL (US)

(72) Inventors: Vitale Kyle Castellano, Auburn, AL (US); Michael Zabala, Auburn, AL (US); Thomas E Burch, Auburn, AL (US); Hayden Burch, Auburn, AL (US); Jonathan Commander, Auburn, AL (US); Kenny V. Brock, Auburn, AL (US)

(73) Assignees: Auburn University, Auburn, AL (US); Edward Via Virginia College of Medicine, Auburn, AL (US)

( * ) Notice: Subject to any disclaimer, the term of this patent is extended or adjusted under 35 U.S.C. 154(b) by 58 days.

(21) Appl. No.: 17/027,464

(22) Filed: Sep. 21, 2020

Related U.S. Application Data

(60) Provisional application No. 62/903,211, filed on Sep. 20, 2019.

(51) Int. Cl.
*A61B 5/00* (2006.01)
(52) U.S. Cl.
CPC .......... *A61B 5/4827* (2013.01); *A61B 5/0053* (2013.01); *A61B 5/6829* (2013.01); *A61B 2560/04* (2013.01)
(58) Field of Classification Search
CPC ... A61B 5/4827; A61B 5/0053; A61B 5/6829; A61B 2560/04
See application file for complete search history.

(56) References Cited

U.S. PATENT DOCUMENTS 9,017,266 B2   4/2015 Leung et al.
2006/0178596 A1* 8/2006 Robichaud .......... A61B 5/4824
                                                    600/553
(Continued)

FOREIGN PATENT DOCUMENTS

GB        2472168 A    1/2011

OTHER PUBLICATIONS

H. Siddiqui, S. R. Alty, M. Spruce and S. E. Dudley, "Automated peripheral neuropathy assessment of diabetic patients using optical imaging and binary processing techniques," 2013 IEEE Point-of-Care Healthcare Technologies (PHT), 2013, pp. 200-203, doi: 10.1109/PHT.2013.6461319. (Year: 2013).*

(Continued)

*Primary Examiner* — Sean P Dougherty
*Assistant Examiner* — Alexander H Connor
(74) *Attorney, Agent, or Firm* — Jacob W Neu; Bradley Arant Boult Cummings, LLP

(57) ABSTRACT

Disclosed herein is a device for repeatably and accurately measuring the threshold sensitivity of the skin on a body part or surface such as the plantar surface of the foot. The machine uses a monofilament pressure test, where a monofilament is applied to the surface of the skin until it buckles at a corresponding force. The device may measure a broad range of pressures and responsive sensation in the patient using multiple applications of the monofilament. The patient indicates a positive or negative response, based on whether the patient sensed the monofilament pressure. The machine may include a foot clamping assembly, a support chassis, a linear motion translation assembly for locating the monofilament at a given position for testing, and a camera for taking images used to identify testing locations and report results. Methods of use and testing protocols are also described herein.

18 Claims, 16 Drawing Sheets

(56) References Cited

U.S. PATENT DOCUMENTS

| | | | | |
|---|---|---|---|---|
| 2008/0193905 A1* | 8/2008 | Leung | ................. | B25J 11/00 |
| | | | | 434/275 |
| 2015/0182158 A1* | 7/2015 | Ino | ................. | A61B 5/4827 |
| | | | | 600/557 |
| 2015/0343632 A1* | 12/2015 | Penn | ................. | B25J 9/023 |
| | | | | 74/490.09 |
| 2019/0021649 A1 | 1/2019 | Van Snellenberg et al. | | |
| 2020/0237259 A1* | 7/2020 | Lopez | ................. | A61B 5/1036 |

OTHER PUBLICATIONS

Chumpon Wilasrusmee et al., A Novel Robotic Monofilament Test for Diabetic Neuropathy, Asian Journal of Surgery, vol. 3, No. 4 (Oct. 2010), pp. 193-198.

Siddiqi U.R. Hafeez et al., Automated Semmes Weinstein monofilament examination replication using optical imaging and mechanical probe assembly, 2015 IEEE 12th International Symposium on Biomedical Imaging (ISBI), New York, NY, 2015, pp. 552-555.

\* cited by examiner

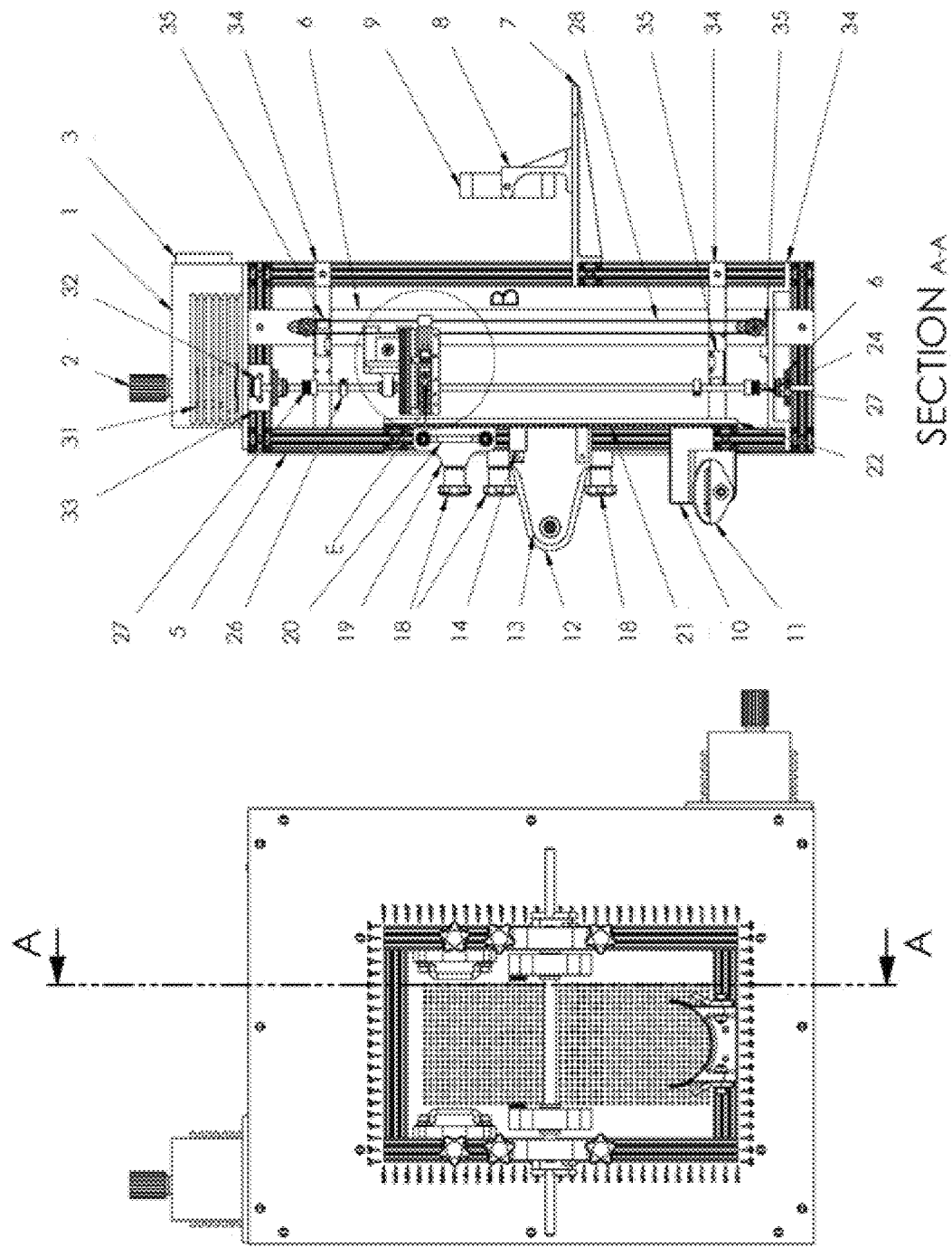

SEMI-AUTOMATED PLANTAR SURFACE SENSATION DETECTION DEVICE

CROSS-REFERENCE TO OTHER APPLICATIONS

This application claims the benefit of filing of U.S. Provisional Patent Application No. 62/903,211, filed on Sep. 20, 2019, and which is incorporated by reference herein.

BACKGROUND OF THE ART

Diabetes is an ever-increasing diagnosis that carries with it numerous neuropathic complications. It is estimated that over 7.5% of adults in the United States have diabetes; this number reaches as high as 30 million Americans with the inclusion of children. It was reported that in 2019, 463 million adults have been reported to suffer from diabetes and it is protected to reach 700 million by 2045.

The cost of care of diabetes is fast approaching $300 billion per year with at least 60% of this cost directed toward hospitalizations and treatment of complications. Neuropathy, sometimes referred to as "diabetic foot", complications are the most common and lead to ulcerations and amputation. The cost of diabetic foot disease is estimated at over $10 billion per year, above the cost of routine diabetic care. Eighty-five percent of all amputations are attributed to preceding foot ulcerations. Some individuals with severe neuropathy may step on a nail and not even feel it. Such injuries, and other less severe injuries, can lead to infections, ulceration, and amputations. An infection or ulceration may start off with just one small part of the foot, but left untended, amputation may be necessary for the entire foot or even of a limb. In fact, a lower limb amputation occurs on average every 30 seconds as a result of neuropathy. Burning feet is one of the most common symptoms found in those who suffer from neuropathy, in addition to shooting pain, an electrical sensation, numbness, and loss of sensation. Ultimately 40 to 60 million people suffer from neuropathy complications.

The standard for evaluation of diabetic feet has traditionally included: foot inspection, checking for peripheral pulses, the ability to detect vibration and ankle reflex, the sensing of pinprick, the ability to distinguish between hot and cold, and the monofilament test. Among these, the monofilament test is most often relied upon and has been occasionally referred to as the "gold standard" of neuropathy assessment. In the monofilament test, monofilaments, made of a single fiber of nylon, and are calibrated to reproduce a consistent buckling stress. Monofilaments (commonly known as Semmes-Weinstein monofilaments) are a popular choice for neuropathy assessment because they are noninvasive, easy to use, quick, and are relatively cheap when compared to other testing methods. The monofilament is applied by hand perpendicular to the skin until it bends or buckles. As the monofilament is inserted the amount of force it produces increases until it buckles. Monofilaments can be sized to apply a desired buckling force, typically measured in grams of force (1 gram of force (1 gF)=9.068 mN). Monofilaments can range from 0.008 to 300 gF, however they are typically expressed using an evaluator size. This buckling force is correlated to an evaluator size, or monofilament gauge, which is a logarithmic relationship between the force applied in gF. For example, the 10-gF monofilament is designated as a 5.07 evaluator. There are 5 classifications of plantar foot surface threshold sensitivity: normal (0.008-0.4 gF), diminished light touch (0.6-2.0 gF), diminished protective sensation (4.0-8.0 gF), loss of protective sensation (10-180 gF), and deep pressure sensation only (300 gF). The 10-gF monofilament is used most extensively to measure an individual's threshold of sensation, as it this value marks the beginning of the loss of protective sensation in individuals. When the monofilament has been properly calibrated it can apply a repeatable force consistently. The 10-gF monofilament has been found to produce repeatable and accurate results.

Despite the extensive use of the monofilament test, it has several drawbacks. A physician may apply the monofilament at too high a speed, thereby applying a greater force than the monofilament is rated for. Additionally, the monofilament may be inserted at an angle. Furthermore, an individual doctor applying the monofilament may not consider the topography of the skin, such as smoothness versus roughness and fatty versus boney surfaces. In addition, monofilaments may differ in length or diameter, or be bent or curved out of the box. Finally, different locations of the foot may be tested at different screenings over time. For all of these reasons, it is impossible to achieve accurate, repeatable measurements that may be tracked over time.

What is needed, then, is a device that can repeatably conduct the monofilament test. Such a machine may also optionally overcome other disadvantages of monofilament testing using hand-applied monofilaments.

SUMMARY OF THE INVENTION

In some respects the invention is directed to a machine for evaluating the presence of neuropathy in a patient, having a testing plate having a first side and a second side and comprising a plurality of holes; a clamp operable to secure the tested area of the patient's skin to the first side of the testing plate; a camera operable to take a photograph of the patient's skin visible through the holes from the second side of the testing plate; a head assembly translatable in an X/Y plane parallel to the second side of the testing plate and comprising a retractable monofilament; and a computer programmed to receive input for selecting a testing location on the patient's skin wherein the testing location is correlated with one of the plurality of holes in the testing plate, position the head assembly over the testing location, and apply the monofilament to the patient's skin at the testing location and at a specified force.

In other respects the invention is directed to a machine for evaluating the presence of neuropathy in a patient, having a testing plate having a first side and a second side and comprising a plurality of holes; means for securing a tested body part of the patient to the first side of the testing plate; means for visually identifying multiple testing locations correlated to a region of the patient's skin visible through the holes from the second side of the testing plate; means for selecting a specified testing location; means for directing a monofilament to be situated over the specified testing location; and means for driving the monofilament against the patient's skin at the specified testing location with a specified force.

In other respects the invention is directed to a method for evaluating the presence of neuropathy in a patient, having the steps of securing a tested body part of the patient to a first side of a testing plate, the testing plate comprising a plurality of holes; taking an image of the tested body part of the patient as viewed from a second side of a testing plate through the plurality of holes; selecting a first testing location, the first testing location correlated to a first region of the tested body part visible through the plurality of holes;

directing a monofilament over the first testing location; and driving the monofilament against the patient's skin at the first testing location with a first specified force.

Other aspects of the invention are described further with respect to the detailed description and the claims.

BRIEF DESCRIPTION OF DRAWINGS

FIG. 9A shows a front profile view of the machine according to an embodiment of the invention.

FIG. 9B shows a section view of the machine taken along line A-A in FIG. 9A.

DETAILED DESCRIPTION

Introductory Information and Definitions

Figure 1:
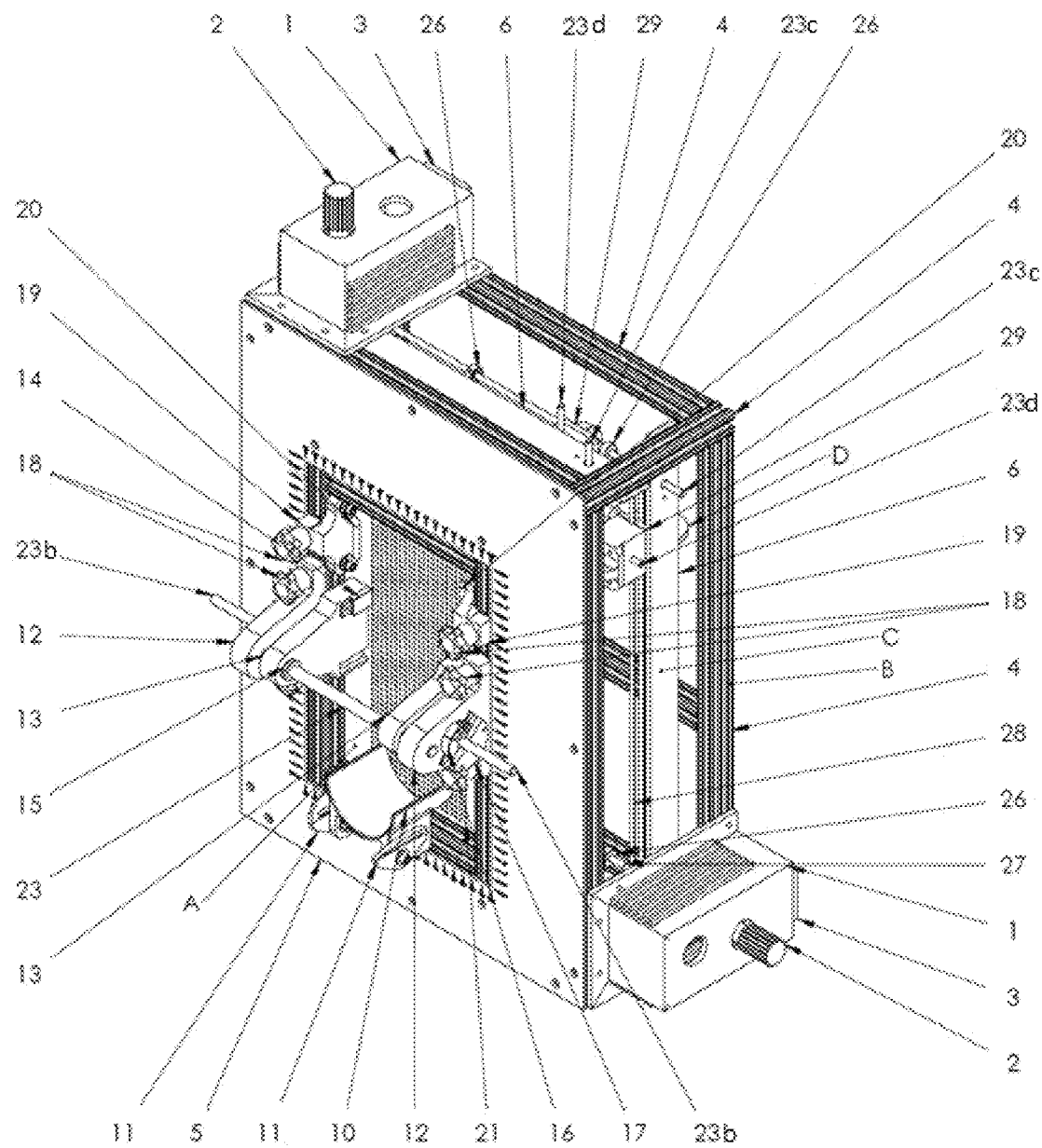
FIG. 1 shows an embodiment of the neuropathy assessment machine shown in an upright, perspective view.

Disclosed herein is a device for measuring the threshold point touch sensitivity of individuals. Single or multiple discrete amounts of noninvasive pressures may be applied at one or multiple locations upon the skin surface of a body part. Locations may be selected for pressure evaluation from an image of the plantar surface against the plate. The sequence of application of the force by a monofilament may be randomized. Patient responses may be recorded, such that a report or depiction of the data, such as a threshold sensation map visually showing the results of the assessment, may be provided.

In describing the embodiments depicted herein, the device will be described as securing a patient's foot for the purpose of testing the plantar surface of the foot (that is, the underside of the foot that contacts the ground). This is because the plantar surface of the foot is a common surface region for developing neuropathy. However, the device may be adapted to secure and test any primary body part or limb of a patient, such as a leg, thigh, arm, or hand to evaluate neuropathic conditions. The primary adaptation needed to make such a device usable with body parts other than a foot is with respect to the clamp apparatus for securing the tested body part (as described with respect to the foot clamp apparatus A below). The remaining assemblies and elements of the device would need only minimal changes if at all. Therefore, while the embodiments will be described herein with reference to the foot as the particular body part being secured, and the plantar surface of the foot as the particular body part being tested, it should be understood that such embodiments may be adapted for testing any desired surface region of the body.

The device is also described as using "noninvasive" testing. "Noninvasive" testing means that the device acts only on the surface of the skin and does not prick, puncture, cut, or otherwise become inserted into the skin.

The device may also be described as "semiautomatic." This means that once set in operation, the device moves automatically to perform one or more sequences of movement or functions, e.g., to move the head assembly to a given location and to drive the monofilament attached thereto, as described further herein. These sequences are punctuated by pauses during which an operator may provide computer instructions or await response from the patient. For example, once the monofilament is driven to provide a given force against the tested location of the skin surface as described herein, the device may pause and await a response by the patient as to whether the force was sensed against the skin. The device may then perform the next sequence of movement or functions once a response or instruction has been provided.

As used in this disclosure and the claims, the word "about" when used in reference to a distance means within 10% plus or minus the stated distance. The word "about" when used in reference to a force means the stated force and a unilateral tolerance of 0.5 gF above the stated force. For example, if the stated force is 2.0 gF, then the machine will apply the monofilament until it reaches at least 2.0 gF, but not to exceed 2.5 gF.

A computer may be a uniprocessor or multiprocessor machine. Accordingly, a computer may include one or more processors and, thus, the aforementioned computer system may also include one or more processors. Examples of processors include sequential state machines, microprocessors, microcontrollers, graphics processing units (GPUs), central processing units (CPUs), application processors, digital signal processors (DSPs), reduced instruction set computing (RISC) processors, systems on a chip (SoC), baseband processors, field programmable gate arrays (FPGAs), programmable logic devices (PLDs), gated logic, and other suitable hardware configured to perform the various functionality described throughout this disclosure.

Additionally, the computer may include one or more memories. Accordingly, the aforementioned computer systems may include one or more memories. A memory may include a memory storage device or an addressable storage medium which may include, by way of example, random access memory (RAM), static random access memory (SRAM), dynamic random access memory (DRAM), electronically erasable programmable read-only memory (EEPROM), programmable read-only memory (PROM), erasable programmable read-only memory (EPROM), hard disks, floppy disks, laser disk players, digital video disks, compact disks, video tapes, audio tapes, magnetic recording tracks, magnetic tunnel junction (MTJ) memory, optical memory storage, quantum mechanical storage, electronic networks, and/or other devices or technologies used to store electronic content such as programs and data.

In particular, the one or more memories may store computer executable instructions that, when executed by the one or more processors, cause the one or more processors to implement the procedures and techniques described herein. The one or more processors may be operably associated with the one or more memories so that the computer executable instructions can be provided to the one or more processors for execution. For example, the one or more processors may be operably associated to the one or more memories through one or more buses. Furthermore, the computer may possess or may be operably associated with input devices (e.g., a keyboard, a keypad, controller, a mouse, a microphone, a touch screen, a sensor) and output devices such as (e.g., a computer screen, printer, or a speaker).

The computer may execute an appropriate operating system such as LINUX®, UNIX®, MICROSOFT® WINDOWS®, APPLE® MACOS®, IBM® OS/2®, ANDROID®, and PALM® OS, and/or the like. The computer may advantageously be equipped with a network communication device such as a network interface card, a modem, or other network connection device suitable for connecting to one or more networks'.

A computer may advantageously contain control logic, or program logic, or other substrate configuration representing data and instructions, which cause the computer to operate in a specific and predefined manner as, described herein. In particular, the computer programs, when executed, enable a control processor to perform and/or cause the performance of features of the present disclosure. The control logic may advantageously be implemented as one or more modules. The modules may advantageously be configured to reside on the computer memory and execute on the one or more processors. The modules include, but are not limited to, software or hardware components that perform certain tasks. Thus, a module may include, by way of example, components, such as, software components, processes, functions, subroutines, procedures, attributes, class components, task components, object-oriented software components, segments of program code, drivers, firmware, micro-code, circuitry, data, and the like.

The control logic conventionally includes the manipulation of digital bits by the processor and the maintenance of these bits within memory storage devices resident in one or more of the memory storage devices. Such memory storage devices may impose a physical organization upon the collection of stored data bits, which are generally stored by specific electrical or magnetic storage cells.

The control logic generally performs a sequence of computer-executed steps. These steps generally require manipulations of physical quantities. Usually, although not necessarily, these quantities take the form of electrical, magnetic, or optical signals capable of being stored, transferred, combined, compared, or otherwise manipulated. It is conventional for those skilled in the art to refer to these signals as bits, values, elements, symbols, characters, text, terms, numbers, files, or the like. It should be kept in mind, however, that these and some other terms should be associated with appropriate physical quantities for computer operations, and that these terms are merely conventional labels applied to physical quantities that exist within and during operation of the computer based on designed relationships between these physical quantities and the symbolic values they represent.

It should be understood that manipulations within the computer are often referred to in terms of adding, comparing, moving, searching, or the like, which are often associated with manual operations performed by a human operator. It is to be understood that no involvement of the human operator may be necessary, or even desirable. The operations described herein are machine operations performed in conjunction with the human operator or user that interacts with the computer or computers.

It should also be understood that the programs, modules, processes, methods, and the like, described herein are but an exemplary implementation and are not related, or limited, to any particular computer, apparatus, or computer language. Rather, various types of general-purpose computing machines or devices may be used with programs constructed in accordance with some of the teachings described herein. In some embodiments, very specific computing machines, with specific functionality, may be required. Similarly, it may prove advantageous to construct a specialized apparatus to perform the method steps described herein by way of dedicated computer systems with hard-wired logic or programs stored in nonvolatile memory, such as, by way of example, read-only memory (ROM).

In some embodiments, features of the computer systems can be implemented primarily in hardware using, for example, hardware components such as application specific integrated circuits (ASICs) or field-programmable gated arrays (FPGAs). Implementation of the hardware circuitry will be apparent to persons skilled in the relevant art(s). In yet another embodiment, features of the computer systems can be implemented using a combination of both general-purpose hardware and software.

The Machine And Its Operation

FIG. 1 depicts an exemplary embodiment of the neuropathy assessment machine shown in an upright, perspective view. The machine has a foot clamp apparatus A, a chassis B, a linear motion translation assembly C, and a camera assembly D. Each of these are described further in more detail and with reference to additional figures.

The chassis B provides a support structure for the moving or operational elements of the machine. The chassis B may be formed of one or more solid structures to which the operational elements of the machine are attached. The chassis B may take any form or shape desirable. In the embodiment of FIG. 1, the chassis is formed of several support bars 4 that are joined together to form a rectangular prism, such as by bolts, welding, or any other means of securely joining the support bars 4. The chassis formed of the support bars 4 is shown isolated from other elements in FIG. 2. In FIG. 1, the chassis is covered on the foot-facing side by a cover plate 5. The cover plate 5 may be made of any safe solid material. The cover plate 5 may also have gradients or position markers located on the face of the over plate 5 to aid the operator with positioning or relocating the foot within the device. The chassis B may also be covered with exterior cover plates to hide the interior workings of the device from the patient's view or otherwise provide an aesthetically pleasing design.

Also as depicted in FIG. 1, the chassis B may have a large stepper motor 31*a* attached to a support bar 4 for moving the linear motion translation assembly C in a first linear direction. A second large stepper motor 31*b* is also shown in the opposite corner for moving the linear motion translation assembly C in a second linear direction. As shown on the exemplary embodiment of FIG. 1, the large stepper motors 31 provide motion along perpendicular directions. The large stepper motor 31 is used in connection with the linear motion translation assembly C described further below. In the embodiment of FIG. 1 the large stepper motors 31 are each housed within a motor cover 1. A fan 3 may also be provided to ventilate and cool each large stepper motor 31. The large stepper motors 31 may be attached as shown in FIG. 1 to a support bar 4, or they may be attached to the linear motion translation assembly C without being attached to the chassis B.

Figure 2:
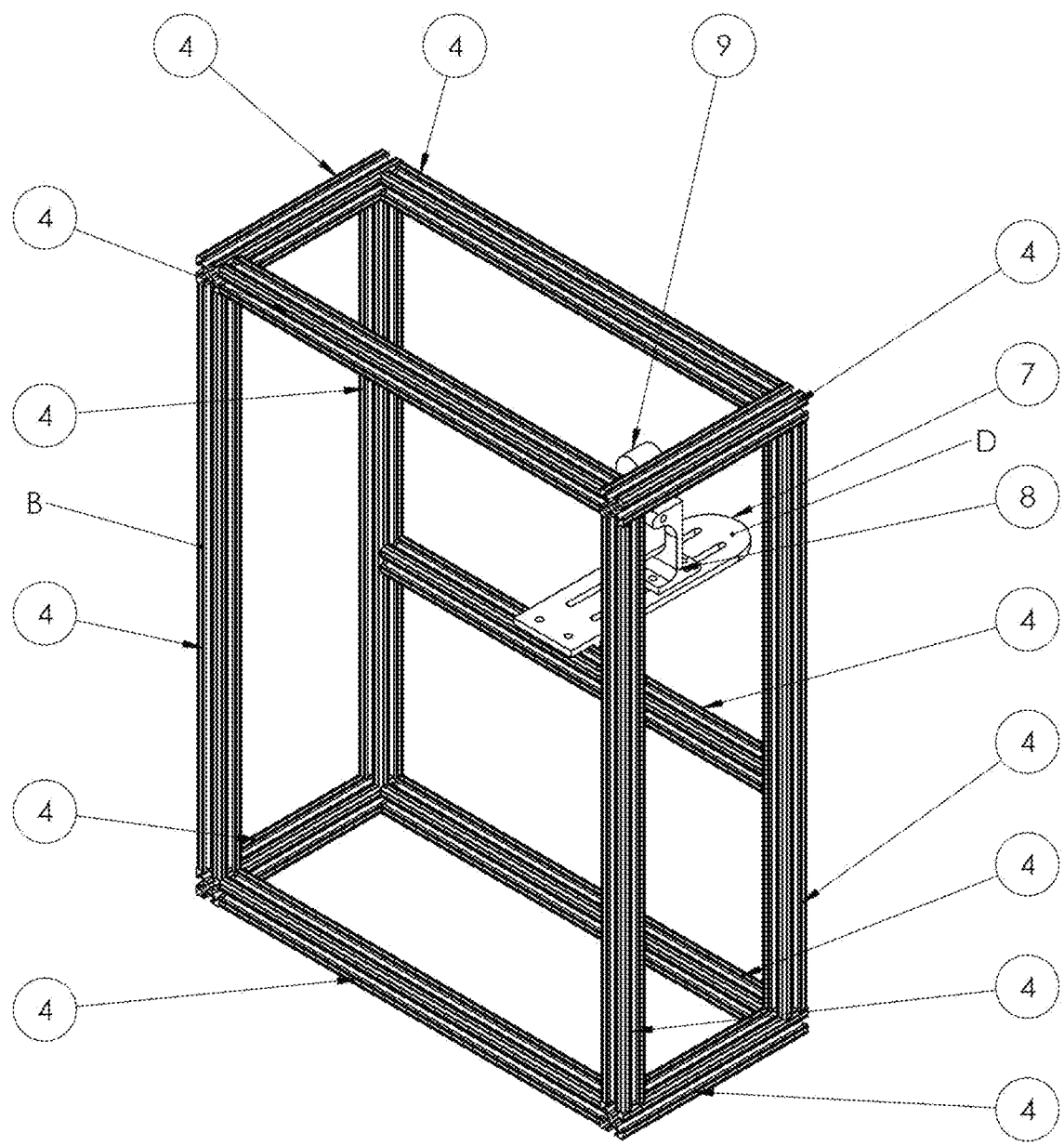
FIG. 2 shows a camera assembly according to an embodiment of the invention.
Figure 3:
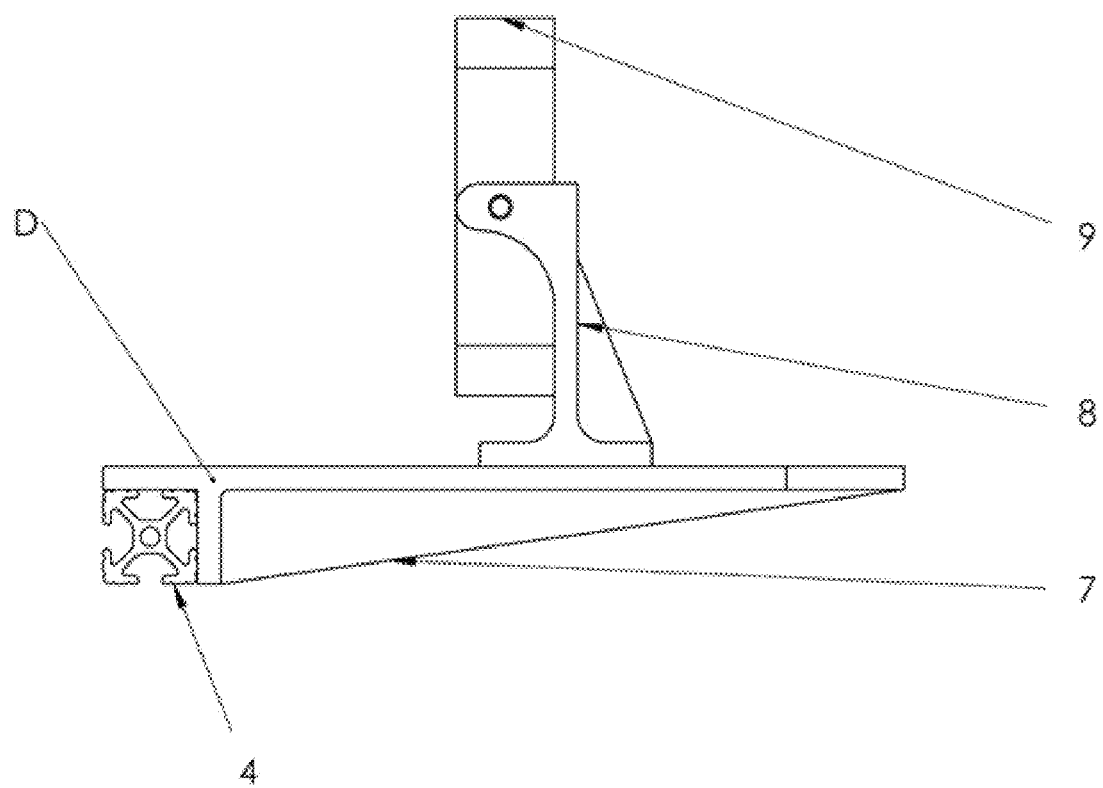
FIG. 3 shows the camera assembly of FIG. 2 in further detail, according to an embodiment of the invention.

FIG. 2 shows a camera assembly D attached to a support bar 4 passing across the middle of one of the large sides of the rectangular prism formed by the chassis B. FIG. 3 depicts the camera assembly D of this embodiment in greater detail. A camera mounting plate 7 is attached to a central location on one of the large sides of the chassis B. The camera mounting plate 7 extends perpendicularly outward from the chassis B. The camera mounting plate 7 supports a camera mount 8, to which is attached a camera 9. The camera 9 is directed back towards the chassis B. The camera 9 is used to take a picture of the plantar surface of the patient's foot as described further below. As depicted in the embodiment of FIG. 1, the camera assembly D is mounted onto the chassis B, which provides the benefit of having a single integrated machine for transport and use. However, the camera assembly D, and in particular the camera 9, may be attached to the chassis B from any desirable surface. Alternatively, the camera 9 may be separated from the chassis B. For example, the camera 9 may be completely independent from the chassis B and moved into and out of place as desired by the machine operator. Accordingly, it is not necessary for the operation of the machine for the camera assembly D to be directly attached to the chassis B as depicted with respect to the exemplary embodiment of FIG. 1. The camera mount 8 may be adjustable along the camera mounting plate 7 to accommodate the size and shape of the camera 9. This allows for placing the camera 9 at the optimal location. The camera 9 takes a photograph of the plantar surface of the patient's foot when placed in the device. Such a photograph may be used to select and record testing locations. Furthermore, a report may be generated at the end of the evaluation by plotting the data on the photograph.

The foot clamp apparatus A secures the foot of the tested patient to the machine. The various clamps and structures of the foot clamp apparatus A are secured to the chassis B. The purpose of the foot clamp apparatus A is to secure and immobilize the patient's foot during the neuropathy assessment. The foot clamp apparatus A may have one or more supports and clamps directed to securing one or more of the patient's lower calf, ankle, heel, metatarsals, or toes. For example, while the methods of assessment described herein are directed to testing for neuropathy across the entire plantar surface of the foot, the machine may be designed to test only the plantar surface of the heel, or only metatarsals, or only the toes, or some combination thereof. If or example only the heel and metatarsals are tested, the toes may not need to be secured.

Using the embodiment as depicted in FIG. 1, the patient may be lying down, such that the patient's heel is resting on a support and the foot extends upward. The machine is arranged upright to be secured to the foot. The plantar surface of the patient's foot rests against the foot plate 21. The foot plate 21 is preferably transparent and has a grid of holes. These holes are used for pinpointing the location of application of the monofilament for use with various foot sizes.

Figure 4:
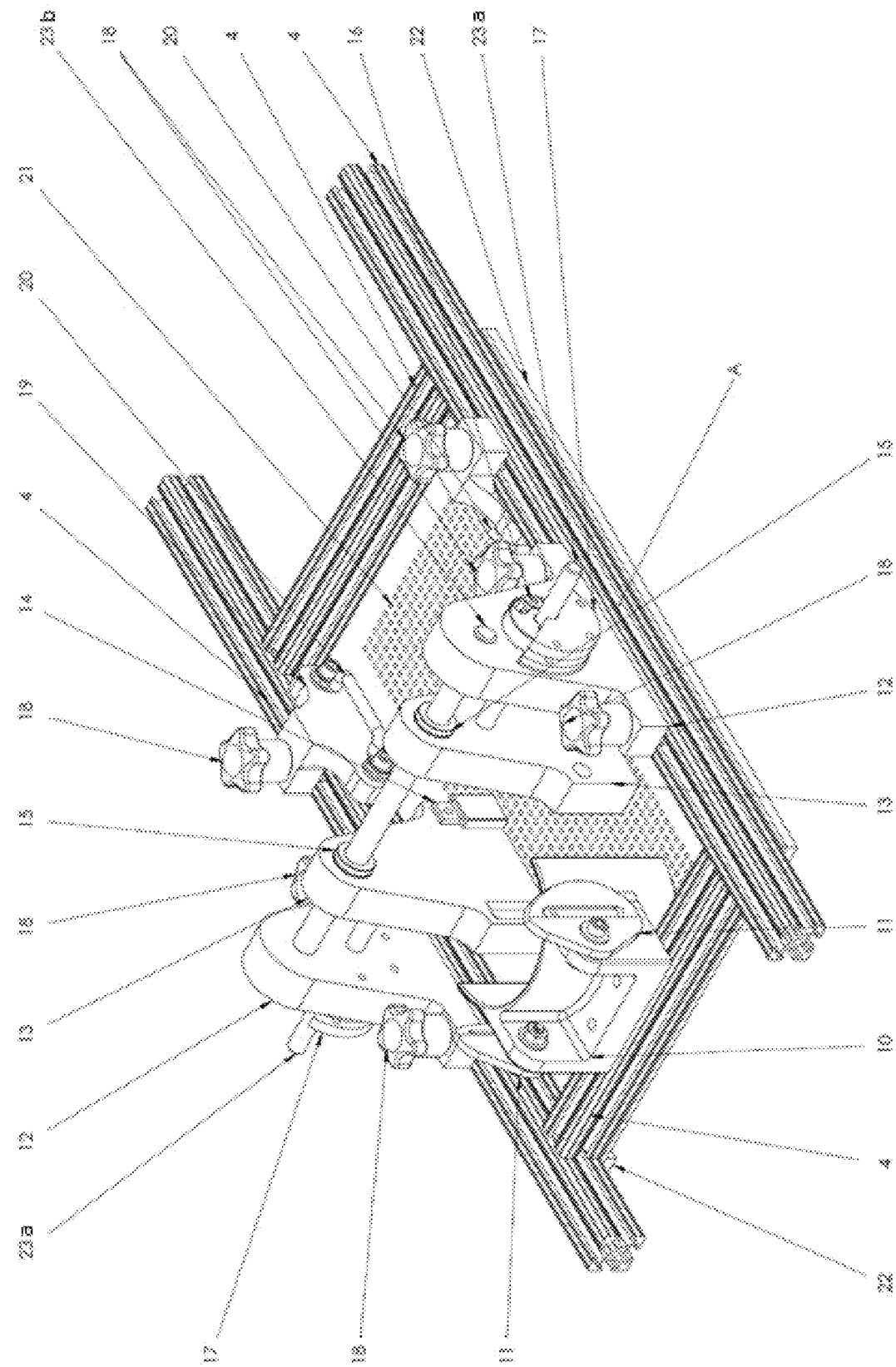
FIG. 4 shows an isolated view of the foot clamping apparatus according to an embodiment of the invention.

To immobilize the foot and prevent ankle rotation, a clamping structure is provided. FIG. 4 shows an isolated view of the foot clamping apparatus A from the exemplary embodiment of FIG. 1. The patient's ankle rests in the ankle support 10. The ankle support is a support plate for holding up the patient's foot during the testing. The ankle support 10 is shown in position here to support the ankle, which is the most ergonomically comfortable and stable part of the patient's leg to be supported. However, the support 10 may also support one or more of the patient's lower calf, ankle, and/or heel. A strap secures and stabilizes the ankle as supported by the ankle support 10. As shown in FIG. 1, the strap may be connected to two strap plates 11, one on each side of the ankle support 10, in order to strap the ankle (or other part of the leg or foot) to the support 10. Preferably, a minimal amount of compression is applied to the ankle by the strap so that the patient does not lose blood flow or pressure sensitivity in the foot during testing.

The clamping structure as shown in the embodiment of FIGS. 1 and 4 has a clamp base 12 and a foot clamp 13. The machine may have one or more clamping structures. The embodiment depicted in FIG. 1 has two clamping structures. The clamp bases 12 are connected to each other by a shaft 23a. A foot clamp 13 houses a sleeve bearing 15 such that the foot clamp is capable of moving linearly along the shaft 23 that connects both clamp bases 12. In this embodiment there are two foot clamps 13. Each foot clamp 13 houses a shaft 23b which interconnects to the clamp base 12 closest to it. The foot clamp 13 and shaft 23b may be locked in place with a clamp lock 16 attached to the clamp base 12. A lock cover 17 applies compression to the clamp lock 16 in order to hold in the clamp base 12. The foot clamp 13 may also have a locator or positioning guide 14 for positioning the foot in the clamping apparatus.

The patient's toes may also be immobilized or pressed against the foot plate 21. In the embodiment of FIG. 1 the patient's toes are compressed by one or more toe clamps 19. Each toe clamp 19 has a foot strap guide 20. A strap is inserted into the foot strap guide 20 and wrapped around or applied against one or more toes to compress the toes against the foot plate 21.

The clamp bases 12 and the toe clamps 19 are secured to the chassis B in a manner that permits the clamp bases 12 and toe clamps 19 that may be unsecured such that the clamps may be adjusted to accommodate different sizes of feet. In the embodiment of FIG. 1 each clamp base 12 and toe clamp 19 are secured to a support bar 4 with lock handles 18. The lock handles 18 may be tightened to secure the clamps to the support 4, or the lock handles may be loosened to adjust the respective clamps to move linearly along the support 4. This allows the clamps to be individually adjusted to provide proper pressure and fit for immobilizing the patient's foot.

FIG. 4 is a close up of the foot clamp apparatus A. Its overall shape is made up of four supports 4. Connected to the supports 4 is the foot plate 21, which houses an array of holes in order to accommodate for different foot sizes. The foot plate 21 is further reinforced by two foot plate support brackets 22, which apply compression to this part and connect to the supports 4. Likewise, this figure also highlights the clamping features of the machine. The ankle support 10 and the ankle strap plates 11 are used to fix the ankle in place during testing. The clamp bases 12, foot clamps 13, and locators 14 are assembled together with shafts 23 and large sleeve bearings 15. When these parts are combined, they create a structure used to keep the foot from rotating by applying minimal compression. This is achieved by using the clamp locks 16 and the lock covers 17. The toes are compressed by an assembly of toe clamps 19 and the foot plate guide 20. The toe clamps 19 and the clamps bases 12 translate linearly along the support 4 and lock in place with the use of lock handles 18. All of these features allowing for varying foot sizes to be tested and also allow for the foot to be reasonable relocated to for future evaluations.

Figure 5:
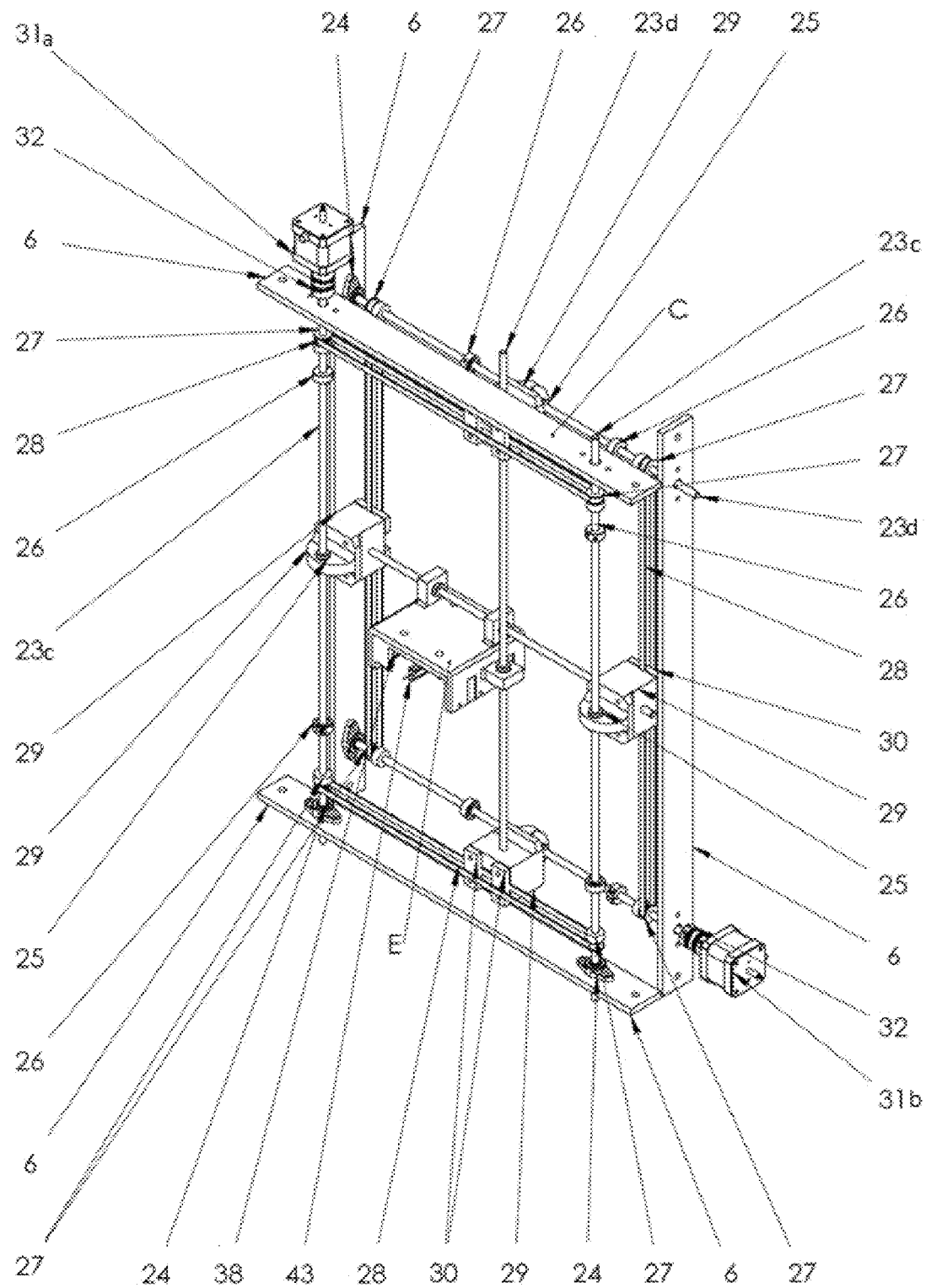
FIG. 5 shows an isolated view of the linear translation assembly according to an embodiment of the invention.

While the embodiment depicted in FIG. 4 shows the foot clamp immovably secured to the chassis B, in other embodiments the foot clamp A may be pivotable with respect to the chassis B such that the foot clamp can be pivoted upward and away from the foot plate 21, thereby creating an open area for unimpeded access for a patient to place a foot on the test plate 21. Once in place, the foot clamp A may be pivoted back down onto the patient's foot to secure the foot for testing. This may be especially desirable for patients with limited mobility The linear motion translation assembly C provides a support and translation apparatus for applying the monofilament 44 for neuropathy testing at the desired location on the patient's foot. The linear translation assembly C is shown in FIG. 1 as a part of the exemplary embodiment depicted therein, and in isolation in FIGS. 5 and 6. The head E, which is a particular subassembly of the linear motion translation assembly C, is further depicted in FIGS. 7, 8A, and 8B.

Figure 6:
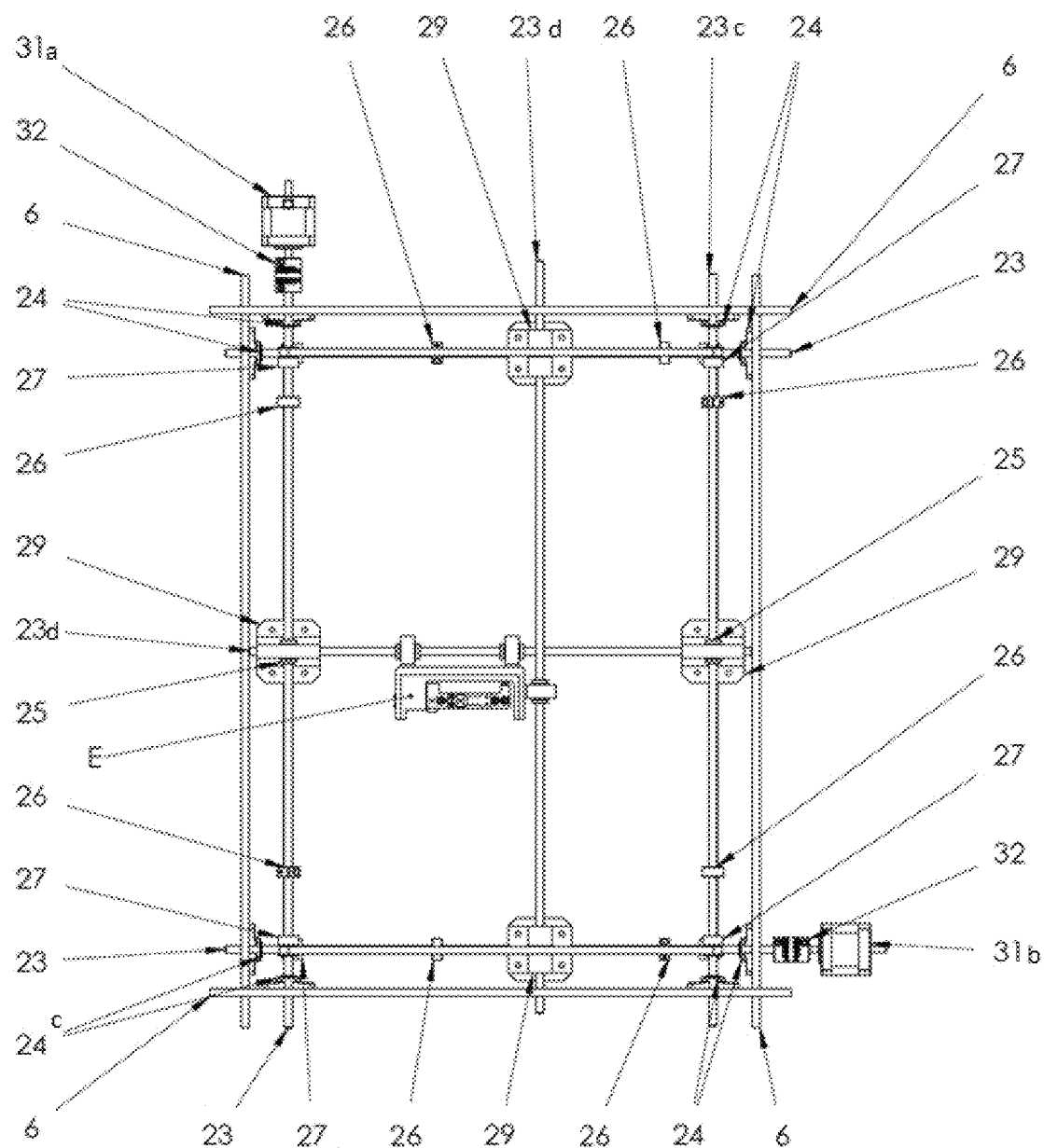
FIG. 6 shows another view of the linear translation assembly according to an embodiment of the invention.

The linear motion translation assembly C is secured to the chassis B by the chassis support plates 6. The chassis support plates 6 may provide additional rigidity to the chassis B. The various components of the linear motion translation assembly C may also be secured to the chassis support plates 6. Bearings 24 are fastened to the chassis support plates 6. First rotary shafts 23c pass through the bearings 24, which permit the shafts to rotate when driven by the large stepper motors 31a and 31b. The rotary shaft 23c driven by large stepper motor 31a is located along a first side of the chassis B, and the rotary shaft 23c driven by large stepper motor 31b is located along a second side of the chassis B, which is perpendicular to the first side referenced above in this sentence. The rotary shafts 23c are connected to the large stepper motors 31a and 31b by motor couplings 32. In order to turn the rotary motion of the large stepper motors 31a and 31b into linear motion, a second rotary shaft 23d is placed parallel to each first rotary shaft 23c and on the opposite side of the chassis B of its paired first rotary shaft 23c. The shafts 23c and 23d in each pair are connected to each other by pulleys 27 and belts 28. In addition, each rotary shaft 23c and 23d has an X/Y axis connector 29 encompassing the body of the shaft with the shaft passing through head sleeve bearings 25, such that the shaft is free to rotate through the X/Y axis connector 29. Each pair of X/Y axis connectors 29 opposite each other are connected by a non-rotating bar 29b. The two non-rotating bars 29b pass through bearings attached to the head E. The belts 28 are secured to the X/Y axis connectors 29 via the belt tension plates 30. The result is that when one or both of the large stepper motors 31a and 31b are driving their respective rotary shafts 23c, the head E moves proportionally in the X/Y plane in the space over the foot plate 21. In this manner, the head E may be moved to a plethora of desired testing locations on the foot plate 21. Hard stops 26 may be secured near each end of each rotary shaft 23c and 23d to limit the range of motion of the head E. FIG. 6 depicts the linear translation assembly in a vertical planar view.

While the present embodiment depicts the linear translation assembly using belts and pulleys, other methods of automating motion across an X/Y plane may also be used. For example, in some embodiments, lead screws may be used. In other embodiments, guide rails and carriages may be used to stabilize the motion.

Figure 7:
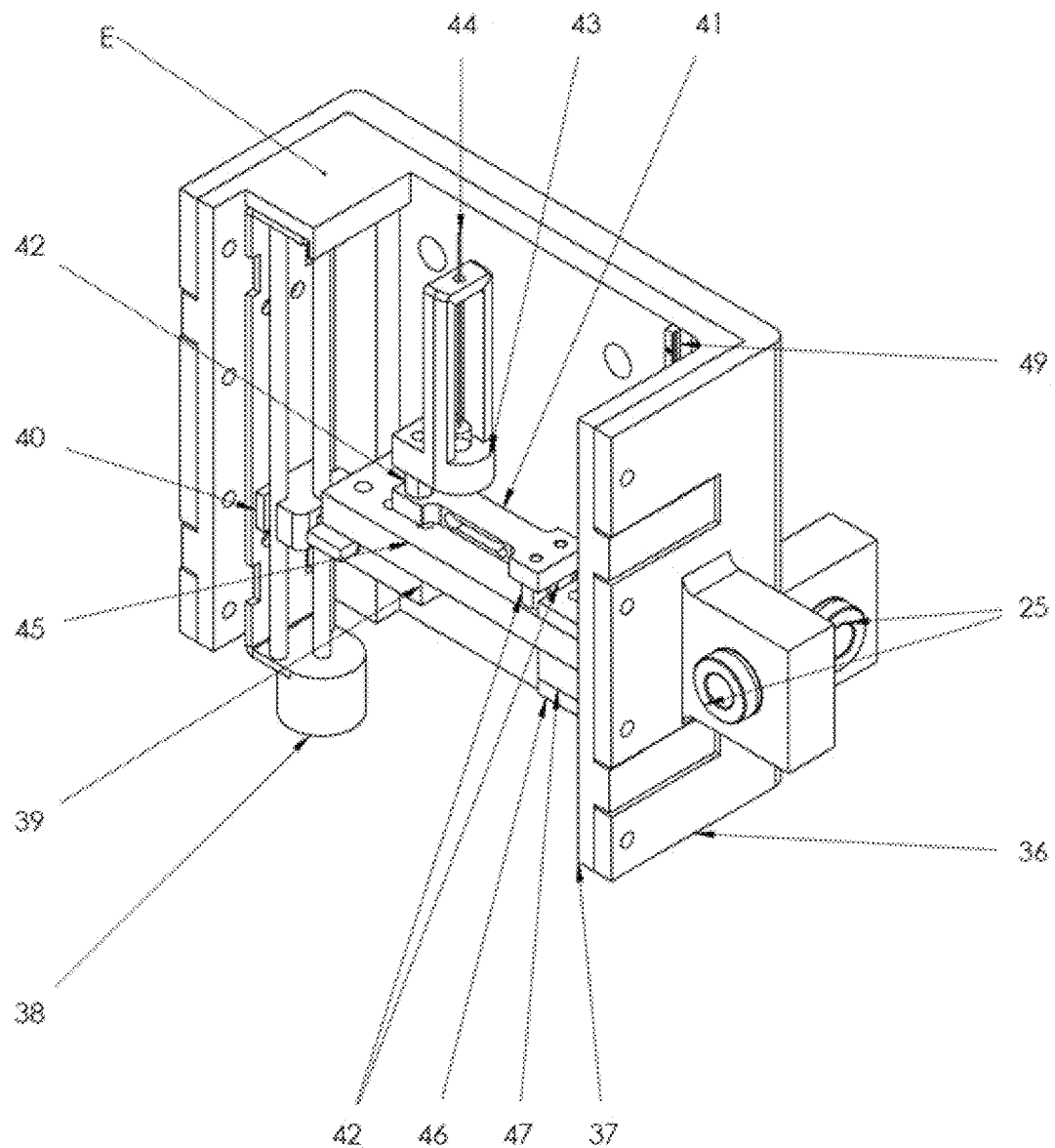
FIG. 7 shows a view of the head assembly according to an embodiment of the invention.
Figure 8A:
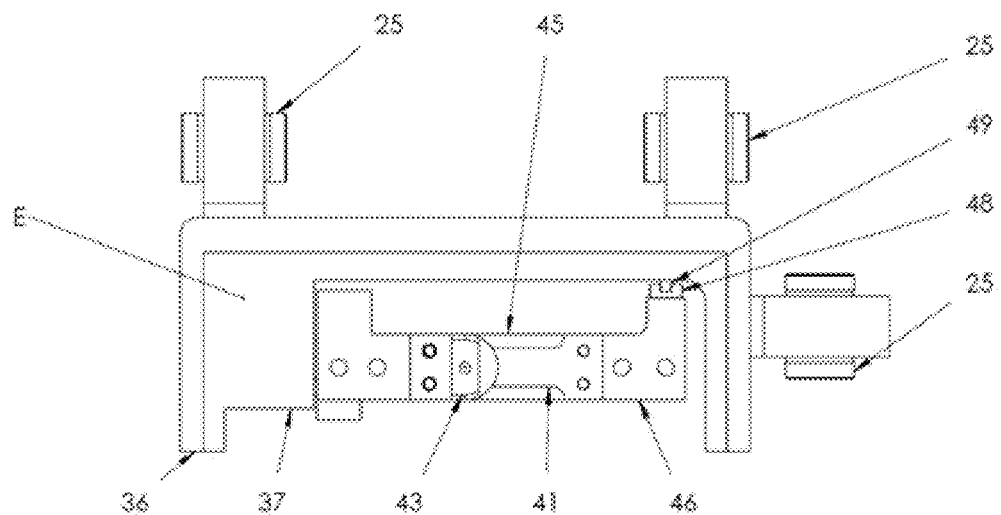
FIGS. 8A and 8B show additional views of the head assembly according to an embodiment of the invention.
Figure 8B:
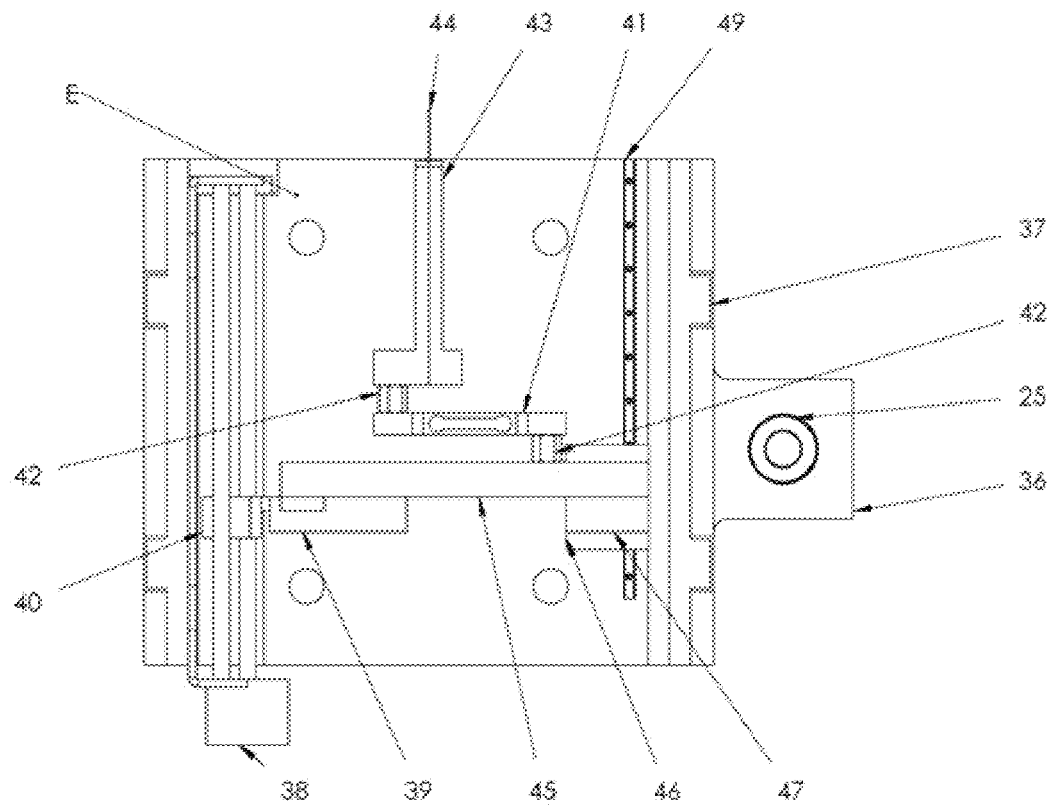

FIG. 7 depicts a close-up view of the head E. A head connector 36 has sleeve bearings 25, through which pass the bars 29b connecting the X/Y axis connectors 29. The remaining components of the head E are secured to the head connector 36. A head chassis 37 fastens to the head connector 36 and houses a small stepper motor 38. The small stepper motor 38 is attached to a lead screw 38b which converts rotation movement to linear movement. A slider 40 is driven by the small stepper motor 38. Attached to the slider 40 is a load cell connector 45. A monofilament support connector 39, a monofilament support holder 46 and monofilament support plate 47 are used to fasten the load cell connector plate 45 to the slider 40 and the rail 49. This allows for smooth linear motion of the monofilament when it is being inserted noninvasively into the plantar surface of the patient's foot. The load cell 41 uses a Wheatstone bridge as further described below to convert a change in electrical resistance arising from the force applied by the monofilament to the foot to a corresponding change in force. The load cell 41 is secured to the load cell connector plate 45 with standoffs 42. The monofilament 44 is inserted into the monofilament load cell adapter 43, which is also attached to the load cell 41 with additional standoffs 42. FIGS. 8A and 8B provide additional depictions of the head E.

In other embodiments using a belt-and-pulley system or lead screws, other types of motors may also be used, such as a DC motor. DC motors may also be used for the large stepper motors as well.

FIG. 9A shows a front profile view of the machine of the embodiment of FIG. 1. FIG. 9B shows a section view of the machine taken along line A-A in FIG. 9A. The supports 4 form a rectangular prism that houses and protects the linear motion translation assembly C. The motor cover 1 and the fan 3 are positioned in proximity of the large stepper motor 31a, which is housed in the motor cover 1 and ventilated by a fan 3. The large stepper motor 31a is connected to the shaft 23c with the motor coupling 32. The large stepper motor 31a is also affixed to a support bar 4 by a motor mount 33. The rotary shaft 23b drives the pulleys 27 and belts 28 wrapped around the pulleys 27.

The chassis support plates 6 provide rigidity and fastening points for the linear motion translation assembly C. The camera mounting plate 7, camera mount 8, and the camera 9 are all present in this view and connect to a support bar 4. The cover plate 5 attaches to a support bar 4 opposite from the camera 9. The foot plate 21, with the use of the foot plate support bracket 22, is also affixed to a support bar 4. The ankle support 10 and the ankle strap plate 11 are attached to a support bar 4 or to the cover plate 5 and are used to fix the ankle in place. The clamp base 12, foot clamp 13, and the locator 14 similarly are attached to a support bar 4 or the cover plate 5 and prevent the foot from rotating during evaluation. The toe clamp 19 and the foot strap guide 20 similarly are attached to a support bar 4 or the cover plate 5 and prevent toe movement during evaluation. These components are able to translate, can be adjusted for different foot sizes, and can lock in place with the use of lock handles 18.

FIG. 9B further depicts limit switch mounts 34 and limit switches 35. The limit switches 35 may be used in association with a homing sequence run upon machine start up. This homing sequence may be used to position the machine accurately and is preferably run prior to each new evaluation (an evaluation being one or a series of tests on a foot). The limit switches 35 provide an electronic limit to the X/Y motion of the head E based on the linear motion translation assembly C and the motor and pulley systems included therein. Hard stops 26 may be installed as physical limits in combination with or as alternatives to the limit switches 35. Hard stops 26 may also be provided as a physical safety barrier in the event a limit switch 35 fails.

Figure 10:
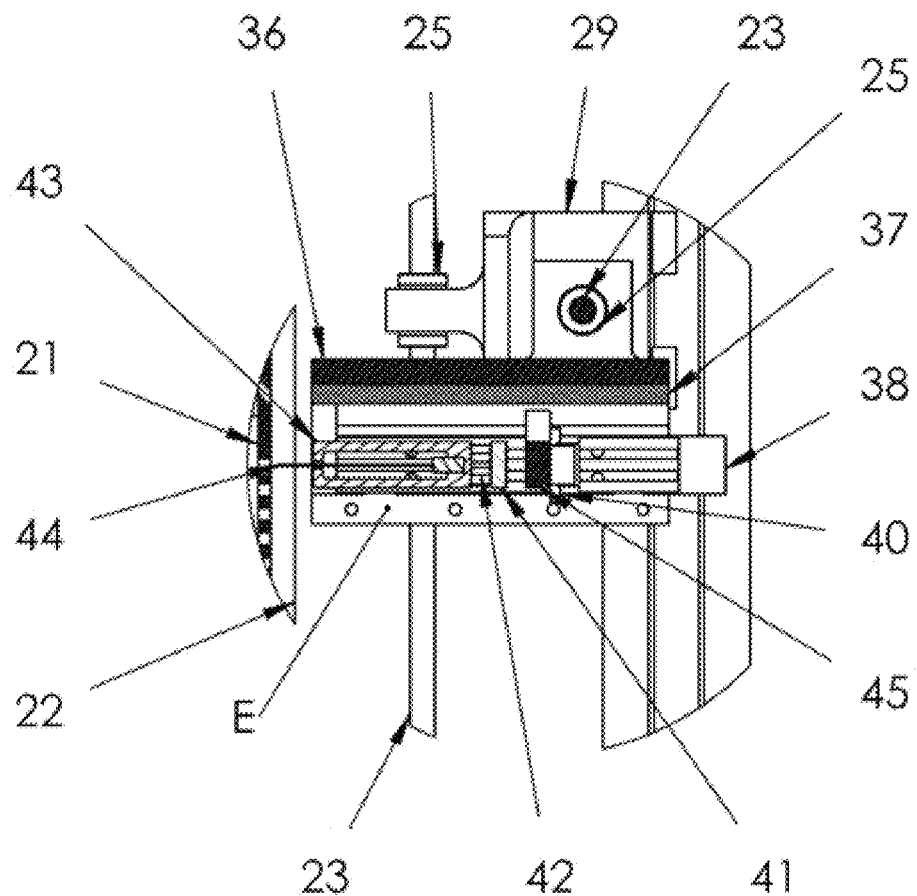
FIG. 10 shows a plan view detail of head assembly and the foot plate according to an embodiment of the invention.

FIG. 10 shows a plan view detail of head E and the foot plate 21. As described above, the foot plate 21 has numerous small holes. These holes are preferably arranged in an X/Y grid. Once the head E is directed to a specific grid location as described further below, the monofilament 44 is driven through the hole at that location to be noninvasively inserted into the patient's foot. The monofilament 44 is driven by the small stepper motor 38. The small stepper motor 38 is secured to the head chassis 37. Again, a DC motor or other type of motor may be used in other embodiments. The slider 40 converts the rotational movement of the small stepper motor 38 lead screw into linear translation. The slider 40 also connects to the load cell connector plate 45 to provide a stable platform for securing the load cell 41 with the use of standoffs 42. The load cell 41 is then attached to the monofilament load cell adapter 43, with standoffs 42, which houses the monofilament 44. Additionally, the head connector 36 utilizes sleeve bearings 25 which glide through shaft 23. This shaft 23 is secured to the X/Y axis connector 29 which also has a sleeve bearing 25 guided through an additional shaft 23.

Figure 11:
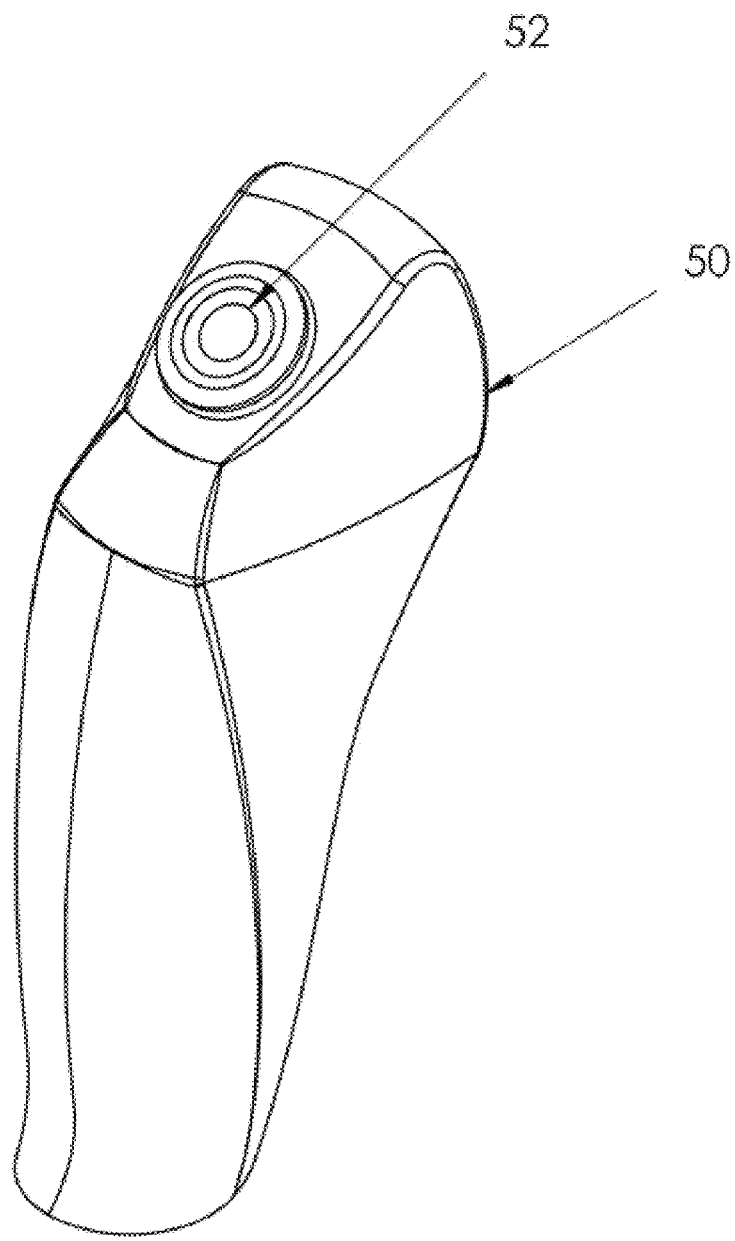
FIG. 11 shows an electronic counter device according to an embodiment of the invention.

In addition to the diagnostic tool, another device is used to receive the patient's responses to the insertion of the monofilament. For example, the patient may verbally inform the operator of a sensation of the monofilament when it was applied, and this may be recorded and stored in a computer as described further below. Alternatively, the patient may respond using an electronic counter device such as that shown in FIG. 11. A handheld counter 50, which is used to collect the patient's response during evaluation. The counter 50 houses a LED pushbutton 52. If the patient experiences the sensation of the monofilament 44 when it is inserted into the foot, the patient depresses the button. In some embodiments the LED may blink a preset period of time (e.g., 5 seconds) during the time when the monofilament 44 is being applied so that the patient knows when to focus on the insertion of the monofilament 44 for any sensation. The counter 50 may be ergonomically designed and hand neutral. It can also be held in multiple ways to accommodate the patient's needs. Other methods of receiving the patient's response may also be used.

Figure 12A:
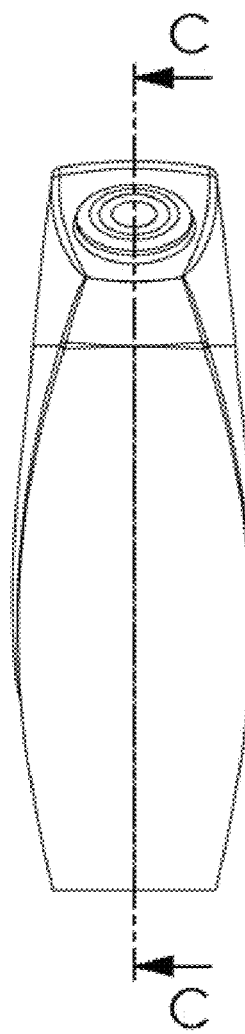
FIG. 12A shows a plan view of a counter device according to an embodiment of the invention.
Figure 12B:
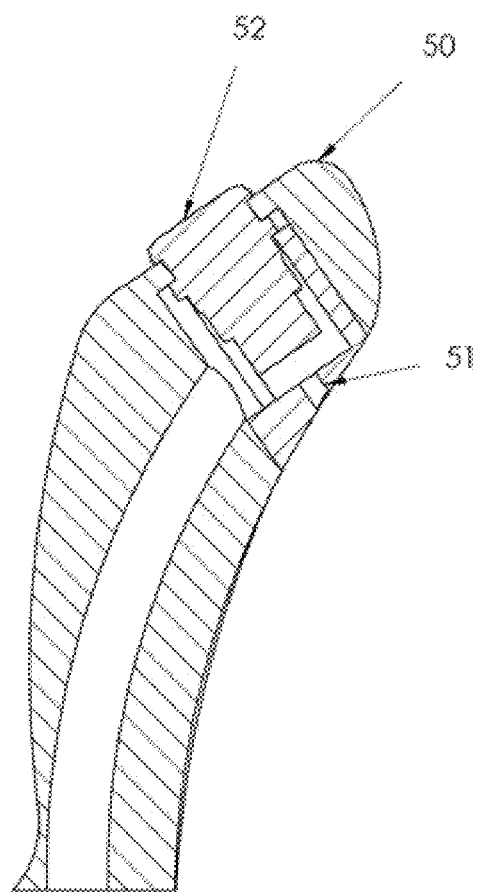
FIG. 12B shows a section view of the counter device along the section line C-C shown in FIG. 12A.

FIG. 12A shows a plan view of the counter 50 with a section line C-C, and FIG. 12B shows a section view of the counter 50 along the section line C-C. of the handle 50. The LED pushbutton 52 is held within the counter 50. A cap 51 is provided on the underside to enclose and hide the counter electronics stored within.

Figure 13:
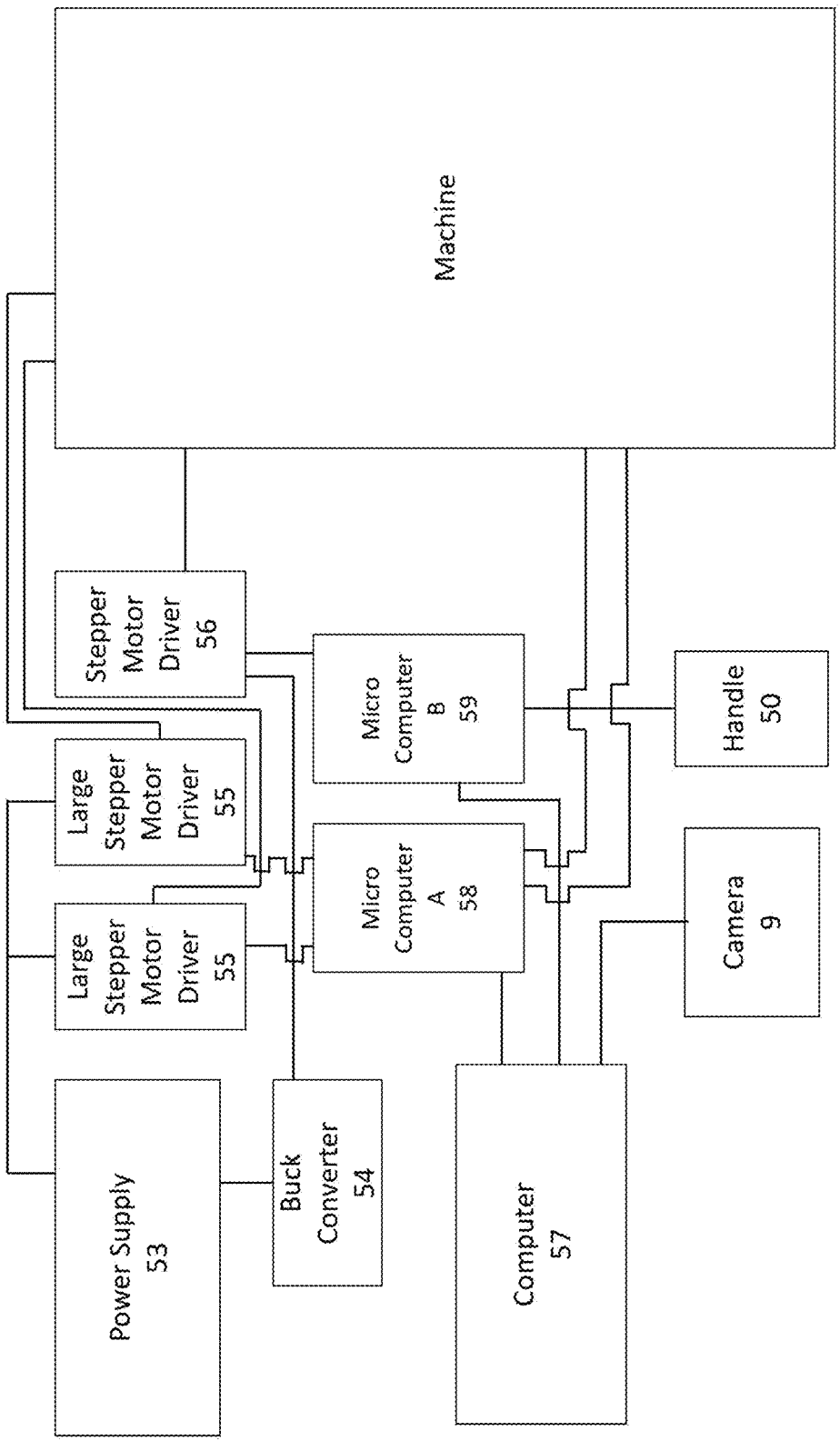
FIG. 13 shows a wiring diagram of the electronic components according to an embodiment of the invention.

The electronic components for operating the machine may be maintained in a box, cabinet, or other container separated from the machine, or they may be integrated onto the machine, such as being attached to a support bar 4. FIG. 13 depicts a wiring diagram of the electronic components for the embodiment of FIG. 1 of the machine. A power supply 53 supplies power for the large stepper motor drivers 55. The power supply 53 is also connected directly to a buck converter 54 which is then used to power the stepper motor driver 56. Alternatively a secondary power supply could be adopted in other embodiments, instead of the buck converter 54. A computer 57 is provided having a processor, a hard drive for storing instructions for operating the device and for storing outputs such as images from the camera 9, user responses from the counter 50, and related load cell data. The computer may also have a display. The computer is connected to microcomputer A 58 and microcomputer B 59. Microcomputer A 58 is used to control the large stepper motor drivers 55. These drivers hook up to the large stepper motors 31a and 31b used for linear translation. Furthermore, the microcomputer A 58 hooks up to the limit switches 35, which are used for the homing sequence and for additional safety features. Microcomputer B 59 directly connects to the stepper motor driver 56 which hooks up to the small stepper motor 38. Small stepper motor 38 assists in inserting the monofilament 44 noninvasively into the foot. Lastly microcomputer B 59 is linked to the counter 50, which houses the LED pushbutton 52. This is used to gather the patient's response following administration of a pressure stimulus. Other wiring designs and component parts may be used to achieve the functions described with respect to the exemplary embodiment.

General Method of Using the Machine for Evaluating Neuropathy in a Patient

Neuropathy symptoms present on a patient's foot may be evaluated using a machine as disclosed herein. The machine moves a monofilament in 3D space in order to apply a pressure stimulus on the plantar surface of the foot. This translation is achieved with the use of stepper motors which when paired with belts and pulleys allow the monofilament to be positioned anywhere within the constraints of the machine.

A patient's foot is secured in the foot clamp apparatus A with the plantar surface of the foot resting against the foot plate 21. The foot plate 21 has a plurality of holes preferably arranged in a grid pattern, through which the monofilament 44 is applied to the foot of the patient. Therefore, each hole in the foot plate 21 corresponds to a potential testing location. These testing locations can be designated by the operator using the computer 57.

Figure 14:
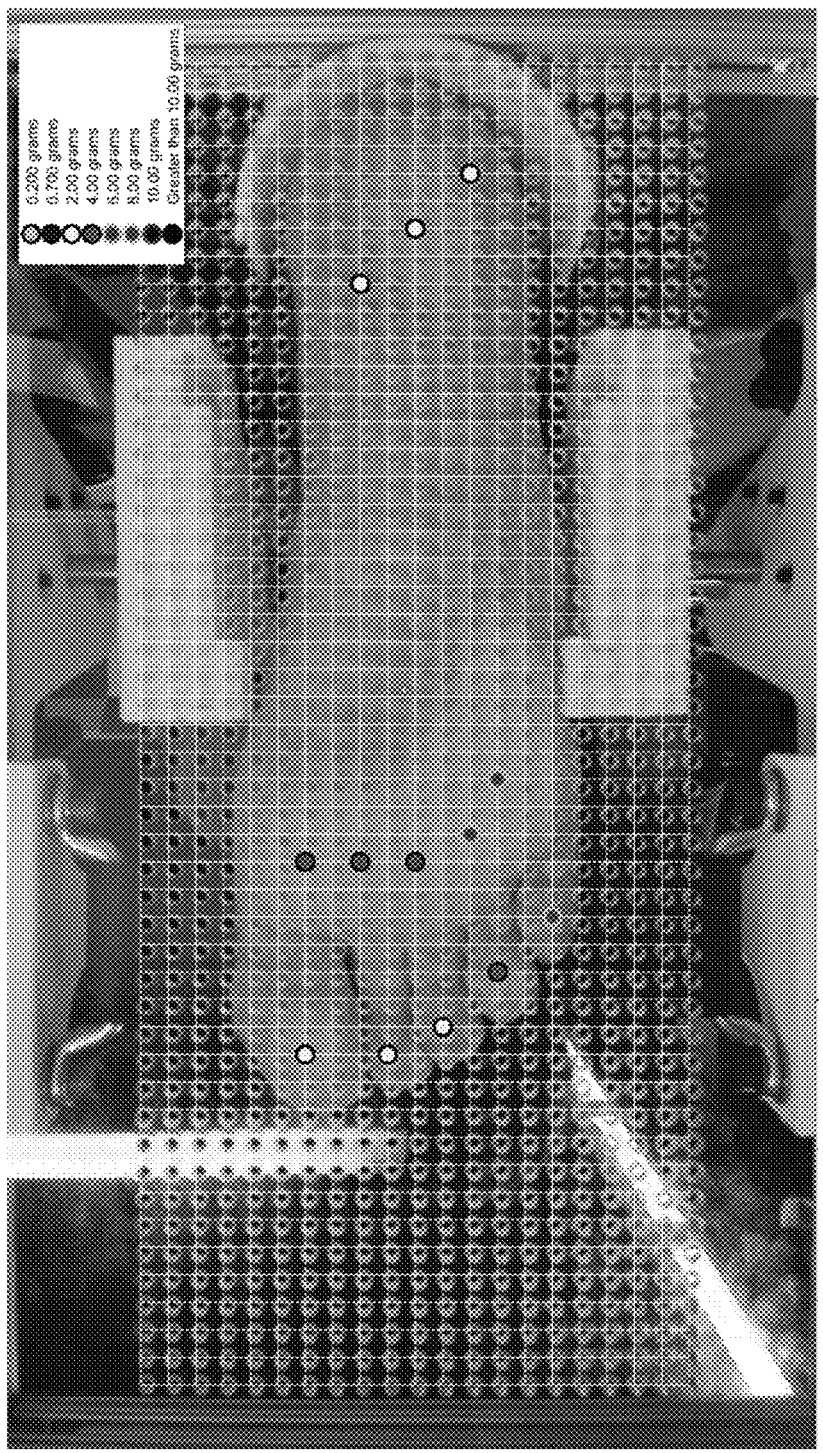
FIG. 14 shows an exemplary image of a foot for testing as taken by the camera according to an embodiment of the invention.

Once the patient's foot is secured, the camera 9 takes a digital photograph of the plantar surface of the foot, which is partially visible through the holes in the foot plate 21. An exemplary image is provided as FIG. 14 showing a patient's foot behind the foot plate 21 but visible through the holes. Using this image as displayed by the computer 57, the operator can select points or regions of the foot for testing by selecting the specific hole locations on the photograph.

The large stepper motors 31a and 31b are calibrated to rotate through a series of uniform, discrete turns or steps such that each discrete step advances the head E to the next hole over in the grid. In this way, the stepper motors 31a and 31b drive the head to the location identified by the operator on the computer 57. Once situated over the proper hole location, the small stepper motor 38 attached to a lead screw is used to drive the monofilament, noninvasively, until it contacts the patient's foot at a prescribed force, as described further herein. The load cell measures the force at which the monofilament is applied. The microcomputer B or the computer provides instructions to drive the monofilament to a prescribed force as measured by the load cell, at which time the small stepper motor 38 stops. In this manner, the machine can be set to apply a desired gram-force amount of force and then retract the monofilament. The machine may be designed to produce between, e.g., 0.2-30 gF using an appropriately rated monofilament. The preferred monofilament for use with the machine is rated to buckle at 10 gF, as the inability to sense a monofilament applied at 10 gF is a medical indicator of loss of protective sensation in the foot. However, different monofilaments, with different lengths, cross sectional areas, and materials can be used to alter this range. To ensure an accurately applied force, the load cell reads at a fast rate and the computer is programmed to slow the insertion of the monofilament until the force applied reaches the desired value. In describing the usage and testing methods below, the testing will be described with respect to a 10 gF monofilament, but it is to be understood that a machine designer or operator could design the machine and testing for a monofilament that has a buckling limit higher or lower than 10 gF without departing from the scope of this disclosure.

When the monofilament is applied to the foot at the desired force, the patient is then prompted to respond with whether they felt the applied force of the monofilament. This may be a verbal request, or the patient may be prompted such as by the LED pushbutton 52 in the counter 50 described with respect to the exemplary embodiment.

The patient's response and the recorded force at the load cell are then recorded for the given location. Additional testing at a given location or at other locations on the foot may follow, as described further herein.

Figure 15:
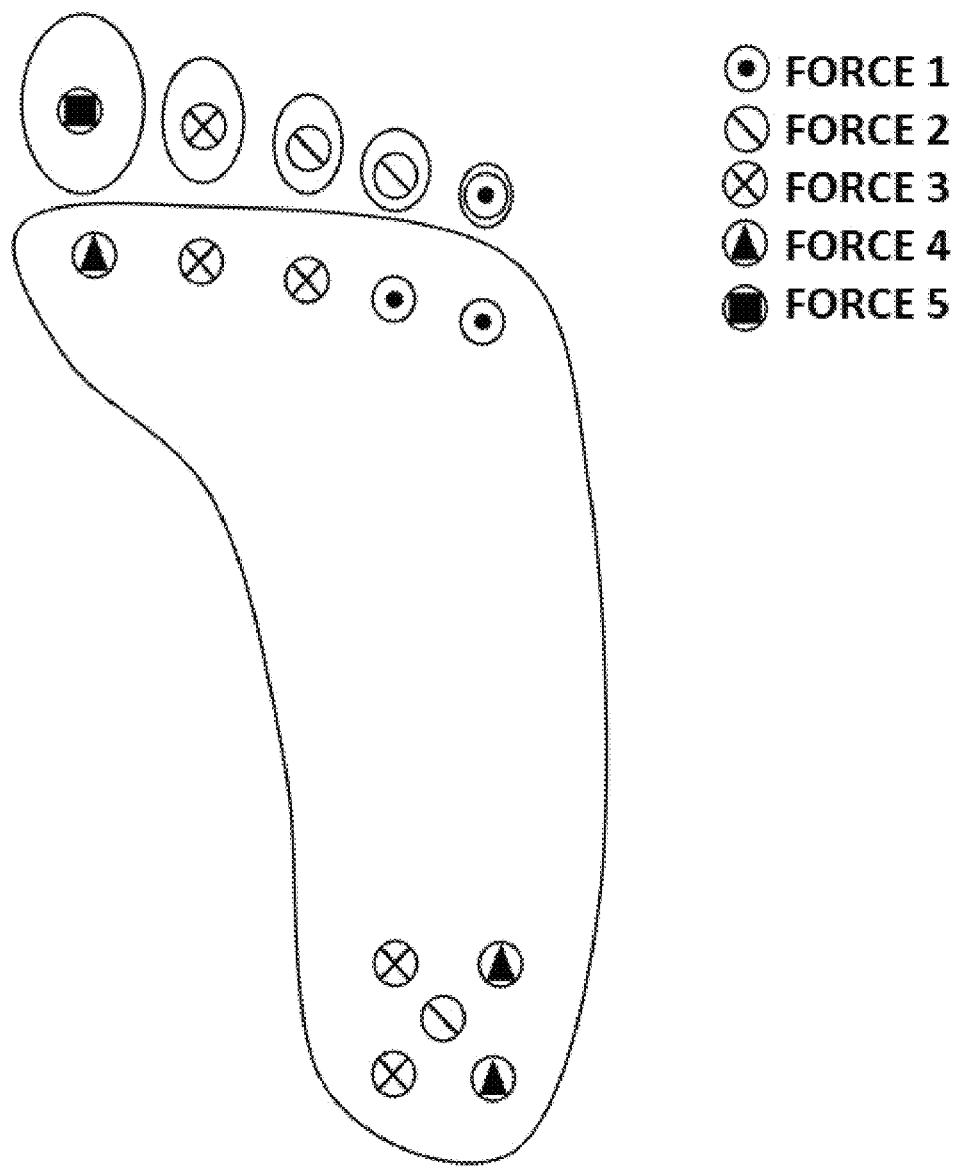
FIG. 15 shows a sensitivity map according to an embodiment of the invention.

Once a patient's threshold of sensation is taken for one or more locations, a sensitivity map, such as that depicted in FIG. 15 may be prepared. Using the image taken of the patient's foot, the magnitude of sensed threshold force can be plotted at each location. This sensitivity map can be used for evaluation and long-term tracking of changes in sensation because it is tied to an image of the actual foot, not an abstract chart or representation. This map can be examined by both the patient and the physician. It also provides a quantitative analysis of the degree of neuropathy present and can be used to monitor changes as part of potential treatments.

Testing Protocols

In addition to the structure of the machine and its general methods of use, the inventors also identified testing protocols for evaluating neuropathy on a patient's foot.

Once the patient places their foot in the machine the computer code provides for taking an image of the patient's foot through the transparent foot plate 21. The image is displayed to the operator. The operator selects locations to be assessed on the foot in order to determine the threshold sensitivity at each testing location. In some testing protocols, the operator selects multiple locations on the foot, including at least one location on a distal phalange, at least one location on a metatarsal head, and at least one location on the heel. In certain protocols, 13 locations may be selected. These locations may include 5 locations on the distal phalanges, 5 locations on the metatarsal heads, and 3 locations on the heel. Once selected, the computer code provides for converting the selected locations from the pixels on the computer display to inches, centimeters, or any other desired unit of measurement. The locations may be rounded to the nearest quarter inch, or such other distances as the holes on the foot plate 21 are separated.

Where locations are selected for multiple regions, the 3 regions will be evaluated one at a time in a specific testing order. The inventors identified four unique testing order paths (Table 1) to test locations in those regions. The selected testing order paths represent the most time efficient order in which the regions are evaluated, based on the relative distance between one another. Other testing order paths, which are not necessarily time efficient, can also be used for assessment.

TABLE 1

Machine Testing Order Paths

| | Testing Order Paths | | | |
|---|---|---|---|---|
| | 1 | 2 | 3 | 4 |
| 1st | Heel | Distal Phalanges | Metatarsal Heads | Heel |
| 2nd | Metatarsal Heads | Metatarsal Heads | Distal Phalanges | Distal Phalanges |
| 3rd | Distal Phalanges | Heel | Heel | Metatarsal Heads |

Furthermore, within each region, the computer program may generate a random testing order for all of the locations within each of the 3 regions so as the patient will not able to predict the order in which locations are accessed. This results in neither the patient nor the operator knowing the testing order, removing any bias from assessment.

The monofilament is then moved into location by the machine and the computer instructs the machine to apply the monofilament at specific loads. The patient will be instructed to press the button 52 if they felt the monofilament and to not push the button if they did not feel it. The patient is given a discrete time, e.g., five seconds, to respond if the patient senses the monofilament pressure. For example, where the counter 50 described above is used, the LED may flash to signal to the user to focus on whether any pressure is being sensed and to click the button 52 if the patient does feel the monofilament. This process is repeated for multiple pressures until the minimum threshold value is determined at the specific location. In some cases the protocol may apply the monofilament at increasing magnitudes of force (0.2, 0.7, 2.0, 4.0, 6.0, 8.0, and 10.0 gF) until the patient can sense the monofilament. Alternatively, the forces may be applied in decreasing levels of magnitude. Applying the monofilament in increasing magnitudes of force would be better suited for a healthy patient, while applying the monofilament in decreasing magnitudes of force would be better suited to individuals who are suspected of already having a loss of protective sensation.

Figure 16:
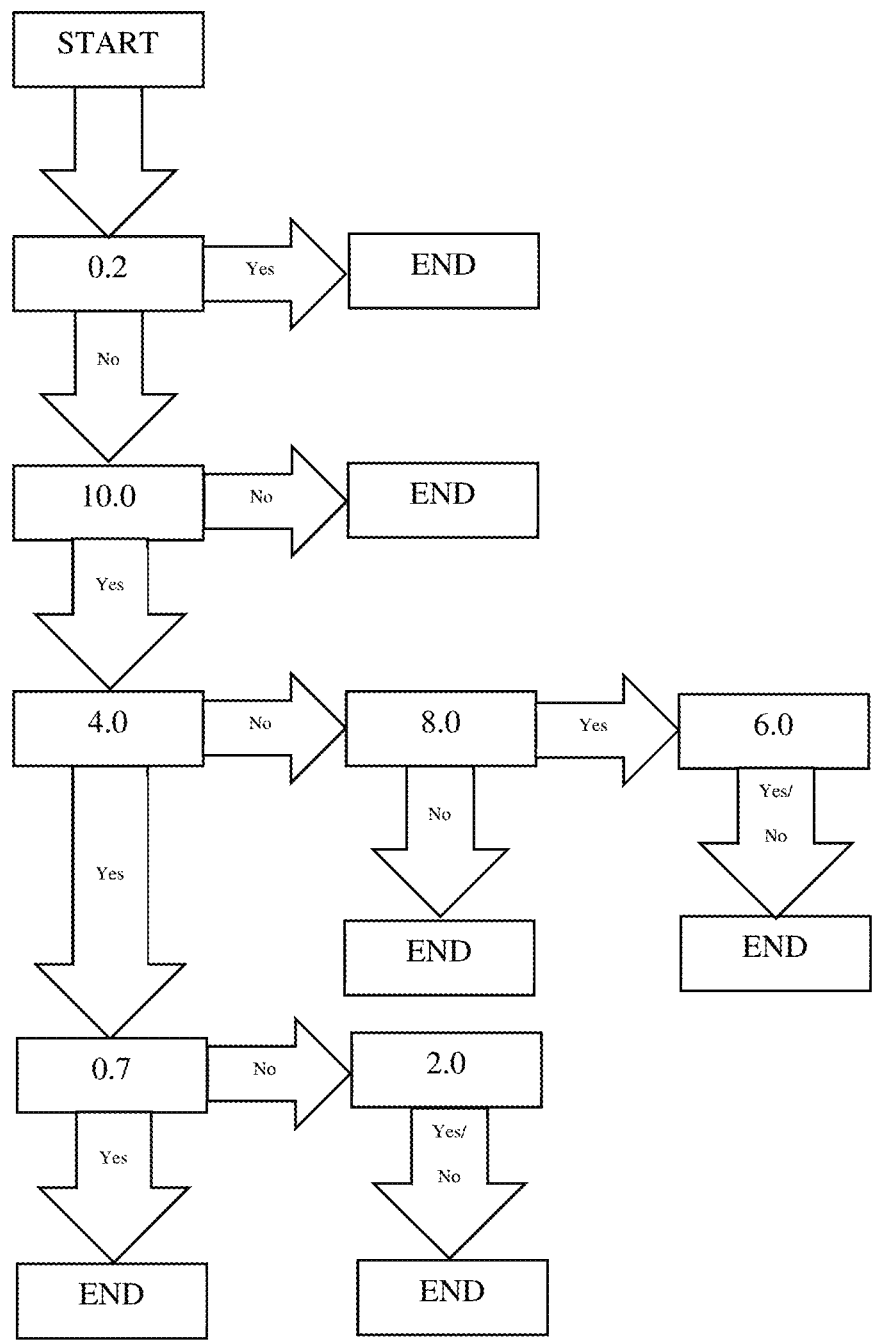
FIG. 16 shows a testing flowchart according to an embodiment of the invention.

In addition to these methods, the inventors also determined that a "homing in" sequence could identify the least amount of sensation perceived by a patient using the least number of applications possible, especially if the patient is in the middle of the threshold sensitivity spectrum or if the patient's sensitivity is unknown. A flowchart of this force testing protocol is provided at FIG. 16. The patient first is asked to respond with a 0.2 gF load applied. If the patient can feel the monofilament, the computer directs the machine to move the monofilament to the next selected testing location. If the patient cannot feel the 0.2 gF then a 10.0 gF is applied. If the patient cannot feel the 10.0 gF then the assessment at this location ends, since they are incapable of sensing the greatest amount of force tested using a 10 gF monofilament. If the patient can feel 10.0 gF, then this will start an iterative process to find what value of force between 0.2 gF and 10.0 gF the patient can sense, according to the flowchart shown in FIG. 16.

In addition, the computer may be programmed to include testing for "false positives" to assess whether the patient is giving inaccurate answers. A false positive will either occur before or after the threshold sensitivity is determined per location. A false positive will prompt the monofilament to move forward but will not contact the individual's skin. This action mimics the sound of an actual application of the monofilament. At the conclusion of a false positive test the LED pushbutton will light up and blink to ask the patient if a force was felt, despite a force not being applied. Alternatively, the patient may be verbally asked whether any sensation was felt if a counter 50 with pushbutton 52 is not provided.

In this methodology a patient with a high degree of sensation loss should complete the assessment in the same amount of time it would take a healthy individual. A patient in the middle between these two spectrums will take more time to complete the assessment, but their time will still be improved by limiting the amount of times the monofilament is applied. Preliminary testing showed that it takes between 7-12 minutes per foot with the above parameters.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

We claim:

1. A machine for evaluating a presence of neuropathy in a patient, comprising:
    a testing plate having a first side and a second side and comprising a plurality of holes;
    a clamp operable to secure a tested area of the patient's skin to the first side of the testing plate;
    a camera operable to take an image of the patient's skin visible through the holes from the second side of the testing plate;
    a head assembly translatable in an X/Y plane parallel to the second side of the testing plate and comprising a retractable monofilament;
    a chassis;
    a linear translation assembly mounted to the chassis and comprising first and second translation motors and a drive train connected to the head assembly, a first rotary shaft driven by the first translation motor and located along a first edge of a second face of the chassis;
    a second rotary shaft driven by the second translation motor and located along a second edge of the second face of the chassis, the second edge being perpendicular to the first edge;
    a first secondary shaft located along a third edge of the second face of the chassis, the third edge being parallel to the first edge;
    a second secondary shaft located along a fourth edge of the second face of the chassis, the fourth edge being parallel to the second edge;
    a first belt wrapped around and connecting the first rotary shaft and the first secondary shaft; and
    a second belt wrapped around and connecting the second rotary shaft and a second secondary belt, wherein the head assembly is connected to the first and second belts such that when the first and second belts are driven by rotation of the first and second translation motors, the head moves in an X/Y plane parallel to the testing plate; and
    a computer programmed to receive input for selecting a testing location on the patient's skin wherein the testing location is correlated with one of the plurality of holes in the testing plate, position the head assembly over the testing location, and
    apply the monofilament to the patient's skin at the testing location and at a specified force.

2. The machine of claim 1, wherein the chassis has a first side to which the testing plate is secured, and a second side opposite the first side to which the head assembly is secured.

3. The machine of claim 1 wherein operation can be semi-automatic.

4. The machine of claim 1 wherein the specified force ranges from about 0.2 to about 30 gF.

5. The machine of claim 1 wherein the specified force ranges from about 0.2 to about 10 gF.

6. The machine of claim 5 wherein the monofilament can be used to apply different forces.

7. The machine of claim 1 wherein the plurality of holes in the testing plate are arranged in a uniform grid.

8. The machine of claim 1 wherein the testing plate is transparent.

9. The machine of claim 1 wherein the camera is mounted to the chassis.

10. The machine of claim 1 wherein the computer is programmed to receive the image and to receive input for selecting a testing location by designating a location on the image.

11. The machine of claim 10 wherein the computer is further programmed to provide an output comprising an image of the patient's skin with force testing information applied at the testing location.

12. The machine of claim 11 wherein the computer is further programmed to store force testing information.

13. The machine of claim 1 wherein the patient's skin being tested is a plantar surface of a foot of the patient.

14. A machine for evaluating a presence of neuropathy in a patient, comprising:
    a testing plate having a first side and a second side and comprising a plurality of holes;
    means for securing a tested body part of the patient to the first side of the testing plate;
    means for visually identifying multiple testing locations correlated to a region of the patient's skin visible through the holes from the second side of the testing plate;

means for selecting a specified testing location;

means for directing a monofilament to be situated over the specified testing location, comprising first and second translation motors and a drive train, a first rotary shaft driven by the first translation motor; a second rotary shaft perpendicular to the first rotary shaft and driven by the second translation motor; a first secondary shaft parallel to the first rotary shaft; a second secondary shaft parallel to the first secondary shaft; a first belt wrapped around and connecting the first rotary shaft and the first secondary shaft; and a second belt wrapped around and connecting the second rotary shaft and a second secondary belt; and means for driving the monofilament against the patient's skin at the specified testing location with a specified force, wherein the means for driving the monofilament is connected to the first and second belts such that when the first and second belts are driven by the first and second translation motors, the means for driving the monofilament moves in an X/Y plane parallel to the testing plate.

15. A method for evaluating a presence of neuropathy in a patient comprising:

securing a tested body part of the patient to a first side of a testing plate, the testing plate comprising a plurality of holes;

taking an image of the tested body part of the patient as viewed from a second side of the testing plate through the plurality of holes;

selecting a first testing location, the first testing location correlated to a first region of the tested body part visible through the plurality of holes;

directing a monofilament over the first testing location, wherein the monofilament is directed by a linear translation assembly comprising first and second translation motors and a drive train for directing the monofilament, a first rotary shaft driven by the first translation motor; a second rotary shaft perpendicular to the first rotary shaft and driven by the second translation motor; a first secondary shaft parallel to the first rotary shaft; a second secondary shaft parallel to the first secondary shaft; a first belt wrapped around and connecting the first rotary shaft and the first secondary shaft; and a second belt wrapped around and connecting the second rotary shaft and a second secondary belt, wherein the monofilament is connected to and directed by the first and second belts in an X/Y plane parallel to the testing plate when the first and second belts are driven by rotation of the first and second translation motors; and driving the monofilament against the patient's skin at the first testing location with a first specified force.

16. The method of claim 15, further comprising steps of receiving at a processor a response from the patient indicating whether the patient sensed the monofilament driven against the skin at the first specified force; and storing the response in computer memory.

17. The method of claim 16, further comprising selecting a second testing location, the second testing location correlated to a second region of the tested body part visible through the plurality of holes; directing the monofilament over the second testing location; and driving the monofilament against the patient's skin at the second testing location with a specified force.

18. The method of claim 17, further comprising steps of receiving at the processor a second response from the patient indicating whether the patient sensed the monofilament driven against the skin at the second testing location and storing the second response in computer memory.

* * * * *